United States Patent
Ullmann

(10) Patent No.: US 8,550,978 B2
(45) Date of Patent: Oct. 8, 2013

(54) SYSTEM FOR AND METHOD OF CONTROLLING PLAYBACK OF AUDIO SIGNALS

(75) Inventor: Paul Ullmann, Vienna (AT)

(73) Assignee: Koninklijke Philips N.V., Eindhoven (NL)

( * ) Notice: Subject to any disclaimer, the term of this patent is extended or adjusted under 35 U.S.C. 154(b) by 830 days.

(21) Appl. No.: 11/719,428

(22) PCT Filed: Nov. 10, 2005

(86) PCT No.: PCT/IB2005/053701
§ 371 (c)(1),
(2), (4) Date: May 16, 2007

(87) PCT Pub. No.: WO2006/054210
PCT Pub. Date: May 26, 2006

(65) Prior Publication Data
US 2009/0149699 A1   Jun. 11, 2009

(30) Foreign Application Priority Data
Nov. 16, 2004 (EP) .................................. 04105809

(51) Int. Cl.
*A61M 21/00* (2006.01)
(52) U.S. Cl.
USPC .......................................................... 600/27
(58) Field of Classification Search
USPC ............. 600/26–28; 340/575; 386/239–262, 386/300–357; 381/61–65, 98–109; 360/8
See application file for complete search history.

(56) References Cited

U.S. PATENT DOCUMENTS

| 3,855,424 | A | * | 12/1974 | Tharmaratnam et al. | 704/258 |
| 4,573,449 | A | * | 3/1986 | Warnke | 600/28 |
| 5,076,281 | A |   | 12/1991 | Gavish |  |
| 5,101,831 | A | * | 4/1992 | Koyama et al. | 600/500 |
| 5,167,610 | A | * | 12/1992 | Kitado et al. | 600/26 |
| 5,215,086 | A | * | 6/1993 | Terry et al. | 607/46 |
| 5,267,942 | A | * | 12/1993 | Saperston | 600/28 |
| 5,304,112 | A | * | 4/1994 | Mrklas et al. | 600/27 |
| 6,123,661 | A | * | 9/2000 | Fukushima et al. | 600/27 |
| 6,554,763 | B1 | * | 4/2003 | Amano et al. | 600/26 |
| 6,702,767 | B1 | * | 3/2004 | Douglas et al. | 601/15 |
| 6,890,304 | B1 | * | 5/2005 | Amano et al. | 600/500 |
| 7,041,049 | B1 | * | 5/2006 | Raniere | 600/26 |
| 2004/0111041 | A1 |   | 6/2004 | Ni et al. |  |
| 2005/0143617 | A1 | * | 6/2005 | Auphan | 600/26 |

FOREIGN PATENT DOCUMENTS

| DE | 3338649 | A1 |   | 5/1985 |
| DE | 4010792 | A1 |   | 10/1991 |
| DE | 4312542 | A1 |   | 10/1993 |
| WO | WO 03096172 | A1 | * | 11/2003 |

* cited by examiner

*Primary Examiner* — Charles A Marmor, II
*Assistant Examiner* — Catherine E Burk

(57) ABSTRACT

A system (1) and method for controlling the reproduction of audio signals via the monitoring of the state of relaxation of a person, wherein at least one physiological characteristic of the person is detected by means of a sensor (14), which characteristic assumes different values depending on different sleep phases of the person and wherein different sleep phases are recognized on the basis of at least one detected changing physiological characteristic by means of an analysis device (19) and wherein the speed for the reproduction of audio signals is changed on the basis of the at least one detected changing physiological characteristic and wherein the reproduction of the audio signals is terminated by a control unit (22) after a certain sleep phase of the person has commenced.

28 Claims, 4 Drawing Sheets

SYSTEM FOR AND METHOD OF CONTROLLING PLAYBACK OF AUDIO SIGNALS

BLOCK OF THE INVENTION

The invention relates to a system and a method for controlling the reproduction of audio signals while monitoring the relaxation state of a person.

BACKGROUND OF THE INVENTION

A configuration is known from the document DE 33 38 649 A, wherein acoustic signals, that is to say audio signals, especially music signals, which are produced by a sound source as sound, especially as music, while a person is falling asleep, are switched off with a delay at a switch-off point in. time after the onset of sleep in dependence on a physiological characteristic of the person. Until this switch-off point in time, reproduction of the audio signals takes place in the way established earlier, which, however, not only sometimes does not have a favorable effect on going to sleep, or generally relaxation, but can even disturb this. Furthermore, switching-off the reproduction of audio signals is mostly noticeable in this—still light—sleep phase, even if the switching-off is effected after a snooze delay when going to sleep and even if the switching-off takes place by reducing the loudness gradually during the reproduction of audio signals, so that the person concerned is unintentionally woken up again.

The known configuration for controlling the reproduction of audio signals is based on the fact that conclusions may be drawn about the various sleep phases on the basis of a physiological characteristic, such as especially on the basis of the breathing rate or pulse rate and that the switching-off is triggered with a delay upon establishing the onset of a certain sleep phase. It should also be noted in this respect that a system for recognizing or discriminating sleep phases or sleep states is described in the document U.S. Pat. No. 5,101, 831 A, wherein especially the pulse rate is utilized as a basis for this recognition. Methods for recognizing the respective sleep phases are thus known. These known methods for recognizing sleep phases can also be used in a system and a method for controlling the reproduction of audio signals.

SUMMARY OF THE INVENTION

It is an object of the invention to propose a system and a method for controlling the reproduction of audio signals while monitoring the state of relaxation of a person, wherein the reproduction of audio signals does not cause any disturbance during relaxation or while going to sleep, but the process of going to sleep is even accelerated by it.

Furthermore, it is an object of the invention to provide a system and a method for controlling the reproduction of audio signals, in which it may be installed in audio systems or audio/video systems at low cost and, furthermore, subsequently be installed in existing audio systems or audio/video systems with comparatively simple means.

Furthermore, it is an object of the invention to detect and transmit the at least one physiological characteristic in a simple manner, in a system and a method for controlling the reproduction of audio signals.

It is also an object of the invention to make it possible to automatically control the reproduction of video signals depending on a monitored state of relaxation of a person, with a system and a method for controlling the reproduction of audio signals.

According to a main aspect of the invention, features of the invention are provided in the system as invented, so that a system as invented can be characterized in the manner indicated below:

System for controlling the reproduction of audio signals via the monitoring of the state of relaxation of a person, which system comprises sensor means for detecting at least one changeable physiological characteristic of the person, which characteristic assumes different values depending on the various sleep phases. of the person and comprises analyzing means for recognizing sleep phases on the basis of the at least one changing physiological characteristic detected by the sensor means and for outputting control information characteristic of the sleep phases and comprises control means, which control means include reproduction-speed control-means that adapted to change the speed for the reproduction of the audio signals on the basis of the at least one detected changing physiological characteristic, and which control means adapted to receive the control information and terminating the reproduction of the audio signals after receipt of control information characteristic of the commencing of a certain sleep phase.

According to a second main aspect of the invention, features of the invention are provided in the system as invented, so that a method as invented can be characterized in the manner indicated below:

Method for controlling the reproduction of audio signals via the monitoring of the state of relaxation of a person, wherein at least one changeable physiological characteristic of the person is detected, which physiological characteristic assumes different values depending upon different sleep phases of the person and wherein sleep phases are recognized on the basis of the detected physiological characteristics and wherein the speed for the reproduction of the audio signals is changed on the basis of the at least one detected changing physiological characteristic and wherein the reproduction of the audio signal is terminated when the commencing of a certain sleep phase is recognized.

In the solutions for controlling the reproduction of audio signals as invented, the reproduction is thus affected by the momentary state of relaxation of the person concerned, wherein the reproduction is changed gradually in respect of the rhythm or clock time and in a preferred case, the audio signal reproduction goes on while becoming slightly slower and slower. The frequency of heartbeat, breathing rate, inhaled air quantity, body temperature, muscular activities of various muscles or parts of muscles and such have proved to be advantageous as physiological characteristics. For example, the average frequency of heartbeat or a frequency that bears a direct relation to the heart rate, or otherwise the average frequency of breathing is monitored to check whether the average heart rate gradually diminishes or possibly remains steady, but does not rise, if the reproduction of the audio signals is slowed down.

If the audio signals are reproduced at an even slower pace without changing the pitch, by for example slowing down the clock or rhythm in the audio signals to match with the physiological characteristic which is also diminishing, particularly the heart rate (pulse rate) and/or the breathing rate slows down, disturbance in the state of relaxation of the person listening to the music will be avoided and this will even aid the process of falling asleep.

In an advantageous solution as invented, the reproduction-speed control-means contain flywheel means for generating an audio-signal reproduction-control information-signal, by means of which it is possible to predefine a reduced speed for the reproduction of audio signals, that is to say a lower clock frequency can be predefined for the reproduction. These flywheel means can be compared to a flywheel oscillator, where a frequency and thus an audio signal reproduction-speed is predefined, which is lowered slowly, for example by 1% to 5% per five (5) minutes. The diminishing speed of the flywheel means can be varied to match the physiological characteristic, preferably a frequency. If, for example, the pulse rate does not fall along with the desired relaxation, or not to an expected extent, the flywheel means can again be matched to the current pulse rate, that is to say raised in respect of the generated frequency and then reduced more slowly than before, so as to match the slowing down of the reproduction of the audio signals to the lowering of the heart rate and/or breathing rate in the manner of a "pacing and leading" principle. In a comparable manner, it could be necessary to raise the audio signal reproduction speed, if the reproduction of audio signals has been taking place too slowly from the beginning. For controlling the reproduction of audio signals as invented, the physiological characteristic is thus constantly detected and monitored in respect of a changed parameter, preferably a frequency change, and the reproduction of the audio signals is matched automatically to the parameter, preferably to the frequency, of the physiological characteristic in respect of its speed, more precisely the slowing-down, so as to promote the desired relaxation, in any case not to disturb this relaxation.

The slowing-down or, generally, the change in the speed of reproduction of audio signals can be realized advantageously with the help of digital signal processing means that are contained in the reproduction-speed control-means and are arranged to change or slow down the clock or rhythm of audio signals—which is represented by the audio signal data fed to these digital signal processing means—in dependence on a control information signal fed to a control input of the signal processing means and which is characteristic of a sleep phase, without affecting the pitch of the audio signals, especially music signals.

It is also advantageous if the termination of the reproduction of audio signals; is started not at a fixed point in time (even if delayed on establishing the falling asleep of the person, as in the state of the art), but on recognizing the transition from the first deep sleep phase into the first dream phase (called REM phase, Rapid Eye Movement). This transition can be established in a known manner and with a high degree of certainty by using analyzing means. In comparison with this, the "moment of falling asleep" is more difficult to establish. On recognizing this transition from the initial deep sleep phase to the first dream phase, the analyzing means can generate and output a corresponding signal in order to use the control means to thus trigger termination of the reproduction of the audio signals. Reproduction of the audio signals is preferably not switched off abruptly, but with gradual reduction of loudness, that is to say faded out. It is also necessary here that the reproduction of the audio signals is not terminated until a point in time at which the person is in deep sleep, that is to say if the drop in sound does not disturb the sleep any more.

The above-discussed reduction in loudness of the reproduction of audio signals can be initiated even before that, during the slowing-down of the reproduction of audio signals, by using control means, so as to achieve an ever softer reproduction of audio signal in synchronism with the slowing down of the speed (that is to say of the rhythm or clock).

Apart from the loudness control explained above, it can also be advantageous to provide a continuous change in the sound characteristics during reproduction of the audio signals, in dependence on the detected physiological characteristics. Thus—apart from the gradual reduction in loudness, which can be carried out with the easing away of the registered muscular activity (of the skeleton muscles)—for example a gradual transition from an initially full sound pattern to damping of high and low frequency components is possible, which effects flattening of the sound pattern, which can also contribute effectively to relaxation.

The reduction in loudness can also be effected continuously or semi-continuously, just like sound control. The change is carried out especially in steps—though in very small steps—where the overall change is in steps but looks practically continuous.

Furthermore, a provision can also be made in the solutions as invented, that of combining video signal reproduction with the audio signal reproduction. The video signal reproduction can be effected in a conventional way for example via a screen or otherwise via an image projection. A computer (PC) or a DVD player or even a video recorder can be used as the source for video signals. The video information is taken to mean in the present context especially conventional video information, but also video information for the generation of still frames. In the present case, which deals with personal states of relaxation, relaxing pictures, such as for example clouds, a leafy canopy in the wood, landscape pictures and such motifs can be projected on a projection surface, such as the ceiling of a room over a reclining piece of furniture. In a manner similar to the gradual fading of the sound signal reproduction at the onset of the REM phase, the video signal reproduction can also be faded out here and finally switched off. The video signal reproduction can of course be made on a conventional screen. The speed at which for example still pictures are displayed in succession and other parameters of the video signal reproduction can be coupled directly to the control of the sound signal reproduction. It is further possible to provide a control of the video signal reproduction independent of the sound signal reproduction, where especially the image sequence in the course of video reproduction can be slowed down at a rate different from that of the speed for the reproduction of audio signals. The brightness of the video signal reproduction can also be reduced in another routine, compared to the reduction in loudness of the sound signal reproduction. In any case the video signal reproduction should be faded and terminated more or less at the same time as the sound signal reproduction. Also in respect of the video signal reproduction, the changes made under control can be effected semi-continuously or continuously.

Simple electro-acoustic converters, for example microphones are preferably used as sensor means for detecting the at least one physiological characteristic. The noises caused by the heartbeat and/or muscle movements can be detected by the acoustoelectric method by using such an electro-acoustic converter, while one microphone can suffice for delivering a microphone signal, but two microphones are preferably used, each of which delivering a microphone signal. The two microphone signals can then be transmitted preferably wirelessly by using standard transmission means and the combined, amplified, transmitted signal can then be analyzed in the analyzing means, which can also preferably be realized by using a digital signal processor (DSP) as part of an audio system or audio/video system. If there are two (or even more) microphones, it is advantageous that possible signal drops at one of the microphones can be bridged. The sensor means can have conventional microphone amplifiers including an Automatic Gain Control (AGC) circuit. And also signal data compression can be carried out that depends on the respective transmission standard. Conventional technology, such as Bluetooth, WiFi or especially ZigBee (conforming to the technology standard IEEE 802.15.4) can be used for the wireless signal transmission. Instead of a wireless transmission, a wired transmission can be provided, wherein the power supply in the area of the sensor means can be effected through a cable, against which, in the case of a wired transmission, an energy source, for example a network device or a battery is to be provided in the range of the microphones.

If such electro-acoustic converters (microphones) are used, it is also particularly easy to give possible control commands to the system through voice input, such as, say, "louder", "softer", "stop", "next" (music piece), "previous" (music piece) "on", "off", "repeat" and can be recognized. In this manner, a remote control device can be rendered superfluous and an appropriate set of functions can be provided by using microphones as speech input device in combination with conventional speech recognition means.

It has already been mentioned above that the pulse rate or heart rate and/or the breathing rate can be used as a physiological characteristic and be monitored as well as analyzed. In addition, it is also advantageous to detect the irregular noises from voluntary and involuntary muscle movements and to analyze them, in order to achieve additional certainty in the analysis of the physiological factors in a known manner and to be able to draw even better conclusions about the state of relaxation and the sleep phases that have commenced. It is therefore also advantageous with the solutions as invented, if the irregular noises caused by muscle movements can be differentiated in respect of the noises caused by the skeletal muscles on the one hand and noises caused by the digestion system on the other.

The detection of the pulse rate and/or of the heart rate can also be carried out by means of electrically conducting electrodes or of optical sensing devices, as has already been known from the medical technology for a long time.

In a method according to the invention, it has also proven to be very advantageous, if a code representing the sleep quality of the person is generated on the basis of the irregular detected noises caused by the muscle movements and, optionally, the time-related pattern of the pulse rate or of the heart rate and/or the breathing rate. This creates the possibility of making perceivable information about his own sleep quality available to a person using the system as invented. The code can then be reproduced as perceivable information in the form of various code numbers or in the form of various code words.

BRIEF DESCRIPTION OF THE DRAWINGS

These and other aspects of the invention are apparent from and will be elucidated, by way of non-limitative example, with reference to the embodiment(s) described hereinafter.

DESCRIPTION OF PREFERRED EMBODIMENTS

Figure 1:
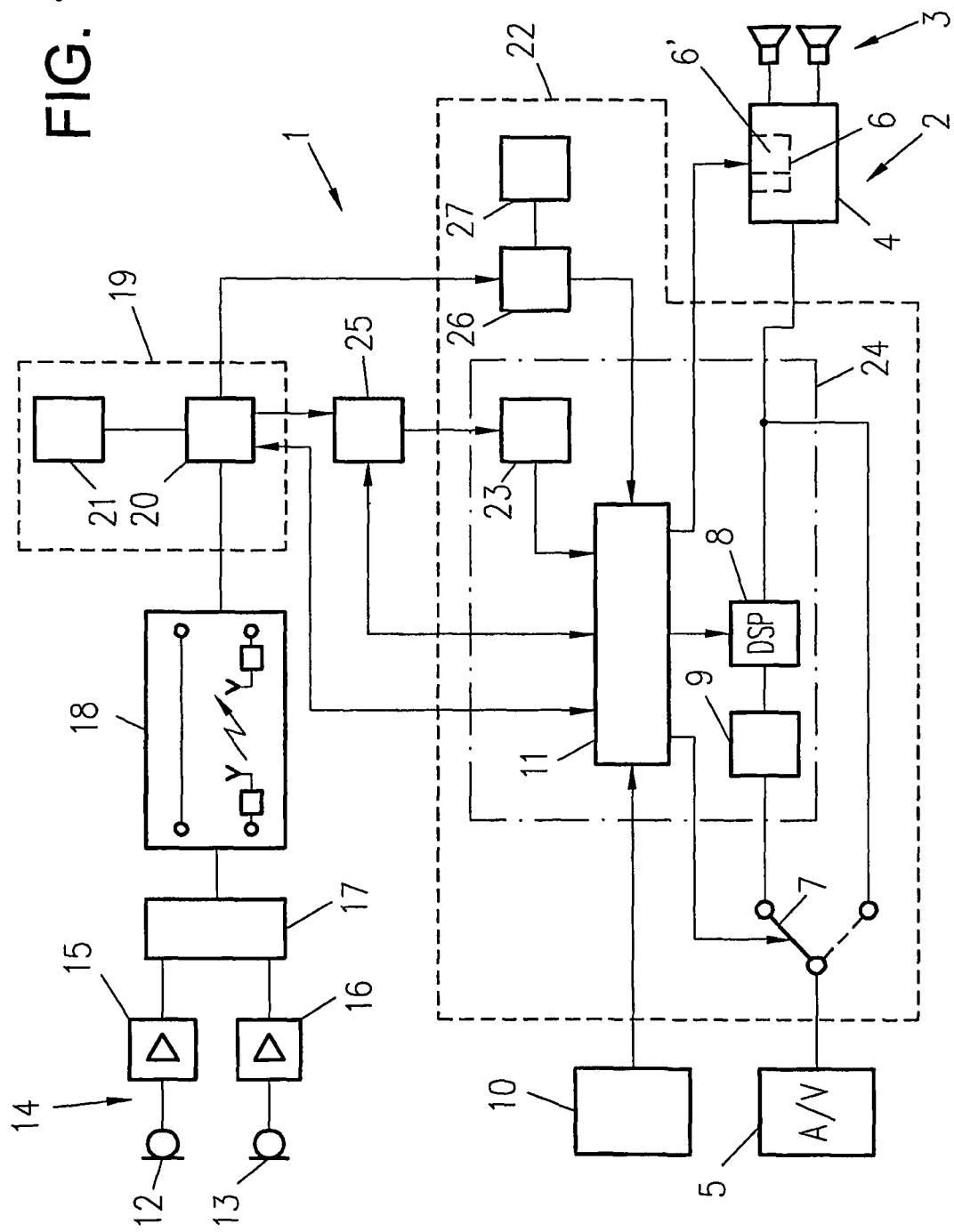
FIG. 1 shows schematically, in the form of a block circuit diagram, a system as. invented for controlling the reproduction of audio signals including an audio signal source and of sound reproduction devices of an audio/video device.

FIG. 1 shows a system 1 for controlling the reproduction of audio signals, actually music signals in the present case, in combination with an audio device or otherwise preferably with an audio/video device 2 including electro-acoustic sound reproduction converters 3, such as loudspeakers and/or headphones, which are connected to amplifying means 4 of the device 2 for reproduction of the audio signals, respectively music signals. The device 2 is of conventional design and it can contain means for playing back audio/video compact discs (CD), SACD, HDD, DVD, magnetic tape cassettes etcetera as a signal source 5. If an analog signal source is available as a source for audio signals, it is assumed that the device 2 also has an AID converter, not shown in more detail in FIG. 1 for converting analog signals into digital signals. On the other hand, the amplifier means 4 contain a D/A converter, which is not further shown, to obtain analog signals for the acoustic reproduction and especially also a conventional sound equalizer 6 shown in FIG. 1 in a broken line including a volume control 6'.

A switch 7 is provided between the actual signal source 5, more precisely between an audio output of this signal source 5 and the amplifier means 4, which switch 7 is in the position shown in a dashed line in the normal operation of the device 2, thus to make possible a normal audio reproduction. In the position of the switch 7 shown in FIG. 1 in a solid line, a signal branch with digital signal processing means 8 and an allocated buffer memory 9 is provided between the actual signal source 5 and the amplifier means 4 to provide a signal processing of the audio signals in terms of slowing down the reproduction in this operating mode of the device 2, that is to say a reduction in the speed or rhythm of the respective piece of music, without affecting the pitch while doing so. The music data already read out at a specified data rate by the signal source 5 are then buffered in the buffer memory, 9 in view of a reduced reproduction data, rate compared to this data rate.

Such a slowing down of the music signal reproduction, or more a general controlling of the music signal reproduction, is realized by the system 1, wherein this , operating mode is changed over to by using input means 10, for example keys and thus, the system 1 is activated. To change over the operating mode, the switch 7 is brought into the corresponding position via control processor means 11. The switch 7 is, as a rule, realized by using an electronic switch, as is done conventionally, so that an elecronic switch over is also possible. The control processor means 11 are provided, for example, by processor means contained in the device 2, especially a microprocessor and they can be used for triggering the digital signal processor means 8 (hereafter also called DSP means, for short) and the amplifier means 4, besides triggering the signal source 5 as well as the switch 7, for the intended control of the music signal reproduction. On the input side, the control processor. means 11 are therefore linked not only to the input means 10, to operate and drive the device 2 in a conventional manner per se, but also to means explained in detail below, to effect the addressed control of the music signal reproduction to match at least one physiological characteristic of a person, if the person so desires and sets the device 2 in this mode.

More in detail, the system 1 hereto contains for example two microphones 12, 13, which are preferably formed by simple condenser microphones and which are placed in a bed area, especially on the underside of a mattress, when the system 1 is used. The sensor means 14 formed by these microphones 12, 13 can further be equipped with associated microphone amplifiers 15, 16, which make a flat physical unit possible, which physical unit can be placed on the underside of a mattress without any problems. Providing two microphones 12, 13 offers greater safety in case of signal failures at one of the microphone arms. The outputs of the microphone amplifiers 15, 16 are funnelled into a filter and converter stage 17, where interfering signal components are filtered out, which arise from undesired ambient noises and where digitization of the amplified microphone signals takes place. Furthermore, signal compression is also possible, depending on the type of transmission, which compression is also a known technique, which is therefore not explained any further here.

The noises picked-up by the microphones 12, 13, which can also be sensed or detected through the mattress, are for example heart or pulse rate, thus a soft and predominantly periodic sound with a frequency of about fifty (50) to eighty (80), especially about sixty (60) beats per minute. Furthermore, a more or less periodic noise (with mainly high-frequency components) of the order of ten (10) actions per minute, which is the breathing rate. Furthermore, there is a relatively loud irregular noise as a result of activities of the skeletal muscle system (voluntary muscles). Further, an irregular noise, which originates from activities of the involuntary muscle system and is caused by the digestive system. From the four signals or characteristics mentioned above, the heartbeat characteristic is the most important, because the chracteristic or its frequency can serve best as a measure for the state of relaxation of the person concerned. The breathing rate can be used at least as an additional characteristic, if the state of relaxation or the sleep phase is monitored. The analyzed breathing rate can additionally be used as a support in the identification of sleep phases or sleep states, in a manner similar to the analysis of the irregular noises, due to the muscle movements of the voluntary and involuntary muscles. Overall, it is possible to draw conclusions about the state of relaxation or the sleep state of the person concerned based on the purely acoustically detected characteristics, without any problems, wherein conventional analysis methods can be applied for this purpose in principle.

This analysis of the electro-acoustic signals is carried out in analyzing means 19 after their transmission via transmission means 18, which transmission means 18 in the present case are adapted for wireless transmission, but possibly they may also be adapted for a wired transmission. The analyzing means 19, besides having an actual analyzing unit 20, also have a memory 21 for storing and reading-out reference data needed in the analysis.

If, as is preferred, the heart rhythm, that is to say the heart rate or pulse rate, is used as a basis for controlling the music signal reproduction, that is to say used as physiological characteristic, a frequency information signal is generated in a conventional manner by using analyzing means 19, such as information corresponding to sixty (60) heartbeats or pulse beats per minute. This information is used as control information for control means 22, which control means 22 include the already mentioned control processor means 11 as well as the digital signal processor means 8 and buffer memory 9, the latter means 8, 9, 11 forming the reproduction-speed control-means 24 together with flywheel means 23. The flywheel means 23 are triggered by the analyzing means 19 and an electronic "virtual" flywheel is formed with the help of these flywheel means 23. The "virtual" flywheel uses the above-mentioned control information of the analyzing means 19 or control information derived from it to create a corresponding oscillation with a long, fading time. In this manner, an extraordinarily high tolerance is achieved against brief disturbances-and distorted or defective measured values, because the flywheel means 23 do not react directly to individual values not fitting into a long-time pattern of heartbeats.

The control information of the analyzing means 19 is preferably fed to the flywheel means 23 via differential means 25, to thus generate frequency information in the flywheel means 23, which, depending on the analyzed frequency, especially pulse rate; represents a frequency value (as default control information for the DSP means 8) that is somewhat smaller than the optimally matched value. If, for example, the pulse rate is sixty (60) beats per minute, and on the other hand a track is played, by for example a CD player in the signal source 5 with a speed of sixty (60) crotchets per minute, then for example, frequency information corresponding to a frequency value of fifty nine (59) or fifty eight (58) units per minute is generated with the help of the flywheel means 23, in order to slow down the reproduction of the track from sixty (60) crotchets per minute to fifty eight (58) crotchets per minute by means of the control processor means 11 or the digital signal processor means 8. Quite generally, a value in the order of magnitude of 1% to about 5% per five (5) minutes has proven to be appropriate for slowing down the reproduction speed for music. If the slowing-down or "braking" of the music signal reproduction is too rapid, this may disturb the relaxation or the process of falling asleep for the person who wishes to use the system 1. If such too rapid braking takes place, this may cause the pulse rate to rise. This rise in frequency may, however, also be used upon recognition by the analyzing means 19 for the purpose of bringing the flywheel means 23 back to the initial frequency and to initiate slowing down the reproduction of music signals, starting from the initial speed, with a lower slowing-down speed that corresponds to a lower percentage value in the clock rates per minute in the track to be reproduced. This may also be initiated, for example, by using control processor means 11, which apply a corresponding control information signal to the differential means 25.

The slowing-down of the reproduction of a track may, on the other hand, have the advantageous effect that as a result the heartbeat or the breathing rate of the person monitored for his/her state of relaxation is also slowed down corresponding to the slowing down of the reproduction of music, which is advantageous for the desired relaxation or for a desired falling asleep.

Moreover, according to a preferred embodiment of the invention, in the event of the monitored person falling asleep, the first deep sleep phase and the first dream phase (REM phase) can be recognized by the analyzing means 19 and a signal characterizing the transition from the first deep sleep phase to the first dream phase is generated by the analyzing means 19, to terminate thereupon for example the reproduction of the music signal through the control processor means 11. For this purpose, the loudness of the reproduced music is first reduced continuously through the volume control 6' and finally the audio signal source 5 can be switched over to a stand-by mode or completely shut down, so that no sound is generated any longer by the device 2, as soon as the person enters the first dream phase (REM-Phase), after which first dream phase the probability is again higher that the person would be woken up by external events. The first dream phase can be recognized for example from relatively irregular breathing or from the absence of signals resulting from actuation of the voluntary muscle system or on the basis of a pulse rate slightly rising again.

As the sensor means 14 are formed by electro-acoustic converters, that is to say microphones 12, 13 in this case, electro-acoustic signals are present which can be analyzed in the analyzing means 19 after transmission via the transmission means 18 also in respect of the presence of any speech information, in which case speech recognition means 26 are used for recognizing commands given by the monitored person by voice inputs through the microphones 12, 13 and passing on corresponding command information to the control processor means 11 for activation of the desired functions. These may be commands listed below for controlling the device 2, such as "louder", "softer", "play back", "stop", "next track", "previous track", "on", "off". Characteristic speech data samples for such control commands are saved in storage means 27, which are assigned to the speech recognition means 26.

On the basis of this possible voice input using the microphones 12, 13, which are provided as sensor means 14 anyway as it is, a conventional remote control is not necessary for the resting person, so that the state of rest of the person is not disturbed by manual operation of a remote control.

When using the system 1, a switchover of the switch 7 into the position shown in solid lines in FIG. 1 is initiated by the person concerned who wants to use the system 1, for example through the input means 10, due to which the system 1 is activated for reproducing the music desired and selected by the person, which originates from the signal source 5. Such a "switchover" can however also be effected by a simple change in DSP parameters, which is more functional if the music data are processed by a digital signal processor (DSP), for example, for the purpose of a data decompression or otherwise for regulating the loudness or sound characteristics. After this switchover, the person is monitored without being touched by the electro-acoustic sensor means 14 only by the reception of acoustic signals in respect of heartbeats (that is heart rate), breathing (that is breathing rate) and voluntary or involuntary and irregular muscle actuations. Electric signals are then received, which are transmitted by the preferably wireless transmission means 18 to the analyzing means 19 and are analyzed with the help of the analyzing means 19, wherein a suitable slowing-down of the reproduction of the music signals is introduced via the flywheel means 23. Any control commands spoken by the person are recognized by the speech recognition means 26, which may be realized in a conventional manner per se, such as a command to reduce the loudness by using the volume control 6' in the sound equalizer 6 ("softer"). Consequently, the person who is lying relaxed on a bed is continuously monitored acoustically and the music signal reproduction is controlled in terms of a slowing-down up to switching off at an ideal point in time, during the transitions between the first deep sleep phase and the first dream phase.

Figure 2:
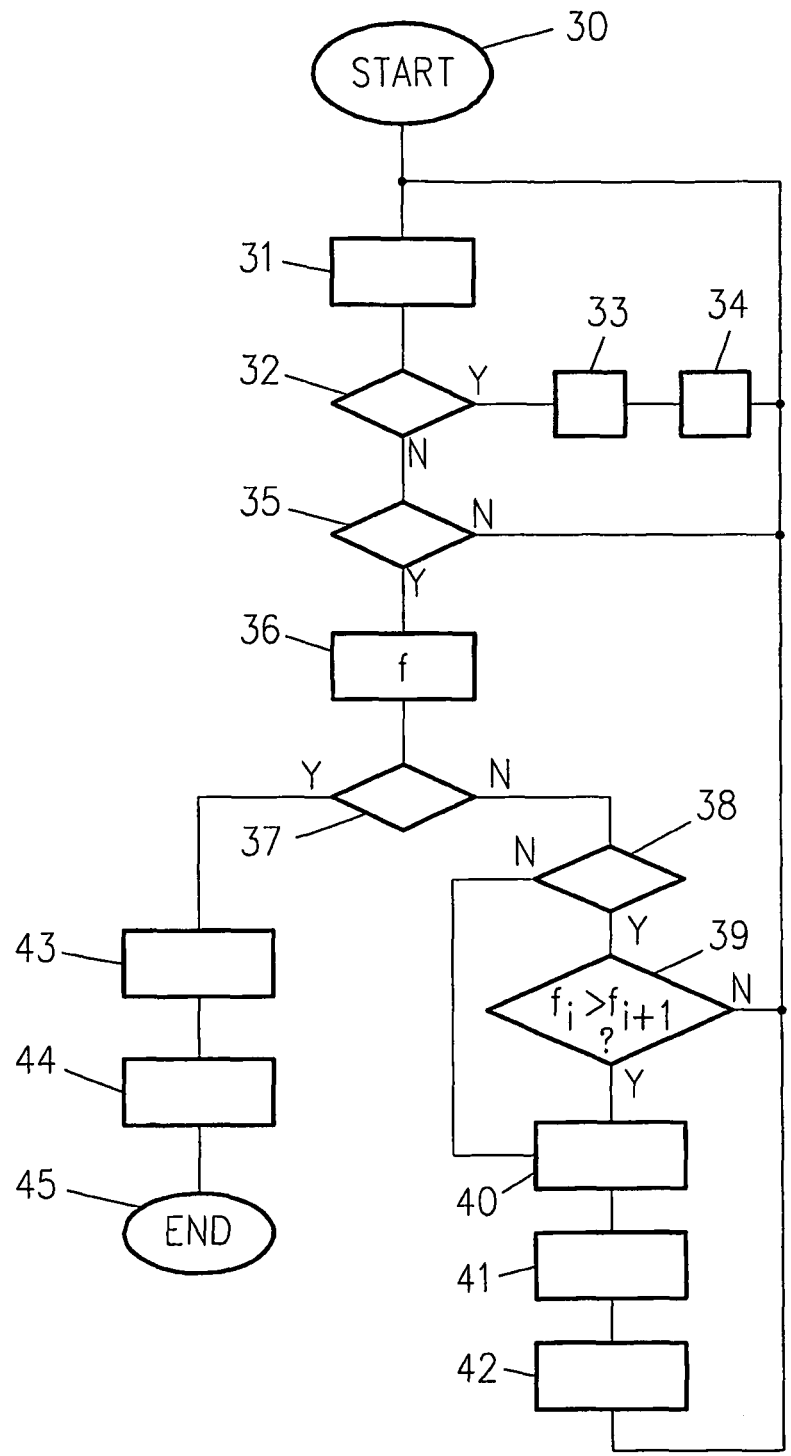
FIG. 2 shows by way of example a process diagram for illustrating-the processes in the control of reproduction of audio signals, wherein the reproduction of audio signals is slowed down to match the relaxation phases up to the sleep phases of a person and is finally terminated.

An example for such a routine is illustrated in FIG. 2 in a flow chart. In this routine, the sensing of sound signals is effected by using sensor means 14 as shown in a block 31 after a starting step according to a block 30, wherein for example the switch 7 is operated and usual initialization steps are taken. Whether the received sound signals are speech signals is checked in the analyzing means 19 according to a check block 32, and if they are, the signals are fed to the speech recognition means 26, as is illustrated in FIG. 2 with a block 33. According to a block 34, the output of a corresponding control command is initiated for the device 2. The routine then returns to the block 31, according to which the received sound is captured.

If it is established in the check block 32 that there is no voice input or not only voice input, there is checked in the analyzing means 19 according to a block 35 whether there is a pulse signal. If there is not, block 31 is returned to. If, however, the presence of a pulse signal is established, the pulse rate is established in the analyzing means 19 according to a block 36. A check is then also done according to a check block 37 whether any transition from a first deep sleep phase to a first dream phase can be established on the basis of this pulse rate or other received sound signals. If it cannot, a check is done in a check block 38, whether a pulse rate has already been saved. If not, then it is checked according to a review block 39, whether the newly determined pulse rate $f_{i+1}$ is smaller or at the most equal to the earlier already saved pulse rate $f_i$. If this is valid, the new pulse rate $f_{i+1}$ is saved, that is to say the old frequency value $f_i$ is replaced by the new frequency value $f_{i+1}$. This is illustrated in FIG. 2 by a block 40. If, however, it is established in the check block 38 that no frequency has yet been saved, the newly established frequency is saved according to the block 40.

If, on the other hand, it is established in the review block 39 that the new frequency is higher than the old frequency, the system returns to the beginning of the routine that is to say to block 31 dealing with the sensing of sound.

If, according to the block 40 the frequency was stored, then subsequently according to a block 41, the described slowing-down ("braking") of the reproduction of music signals is initialized by the flywheel means 23, wherein this is expressed in a reduction of speed of music signal reproduction according to a block 42 (with the help of the DSP means 8). The system then returns to the beginning of the action, that is to say to the block 31.

If it is established in the check block 37 that the person monitored is in the transition phase between the first deep sleep phase and the first dream phase, then first according to a block 43, as shown in FIG. 1 (called "fading out"), a reduction in loudness is initialized through the volume control 6 to terminate the music signal reproduction, after which the reproduction is terminated, say, by switching over of the device to a stand-by position, according to a block 44. The end of the action is then reached according to a block 45.

These and other aspects of the invention are apparent from and will be elucidated, by way of non-limitative example, with reference to the embodiment(s) described hereinafter. Changes and modifications are however possible within the framework of the invention. For example, the speech recognition means 26 may be dispensed with, if no control of the device 2 through voice inputs is needed or desired. The control processor means 11 may be realized, together with the digital signal processor means 8 in a processor module, which can also include the flywheel means 23 and possibly also the analyzing means 19 including the differential means 25. The transmission means 18 provided as the transmission path can effect wired transmission, apart from the preferred wireless transmission, as is illustrated schematically in FIG. 1.

Figure 3:
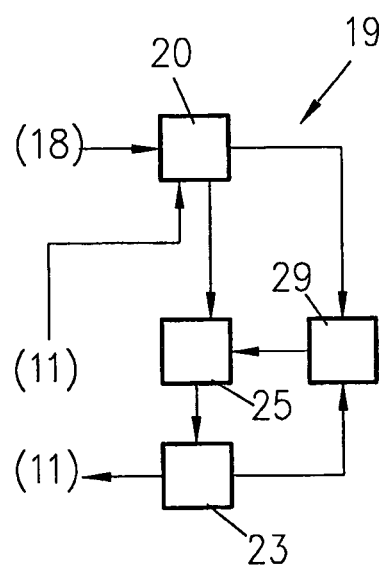
FIG. 3 shows a part of the system as shown in FIG. 1 in a modified embodiment, which part contains the analyzing means for the recognition of the physiological characteristic.

Another modification may for example exist in checking the "frequency reduction" directly with the help of the flywheel means 23 in terms of too sudden braking. Such a modification of the analyzing means 19 and flywheel means 23 is illustrated schematically in FIG. 3. For the sake of simplicity, the memory 21 for the analyzing unit 20 has been left out, but a comparator 29 is shown, which is connected with its inputs to outputs of the analyzing unit 20 as well as of the flywheel means 23, to monitor the difference between the two frequencies, after appropriate adaptation, that is to say conversion to the pulse rate of the flywheel frequency (for the slowing-down of the clock or rhythm of music signal reproduction. On establishing too large a difference, the comparator 29 activates the differential means 25, to reverse the clock control information accordingly, that is to say to activate the flywheel means 23 in terms of a lower "braking" of the music signal reproduction.

The signal source 5 or the device 2 can, as already mentioned, be realized through the most varied audio devices or audio/video devices. The described system 1 is preferably integrated directly in a device 2 provided with such a signal source 5. A CD player, DVD player etc. can be used as signal source 5 as desired. The user of the system 1 is free to choose the music selected for relaxation. It is then possible to play, in the usual manner, several music titles one after the other or in the repeat mode in an endless loop till the music signal reproduction is terminated in the described manner when the specified transition phase between the first deep sleep phase and the first dream phase is entered.

As regards the control of the sound characteristics in the volume control unit 6 described in FIG. 1, a change in the sound characteristics can be additionally or alternatively made via the DSP means 8. DSP means 8 as well as the sound equalizer 6 thus form the sound control means.

Figure 4:
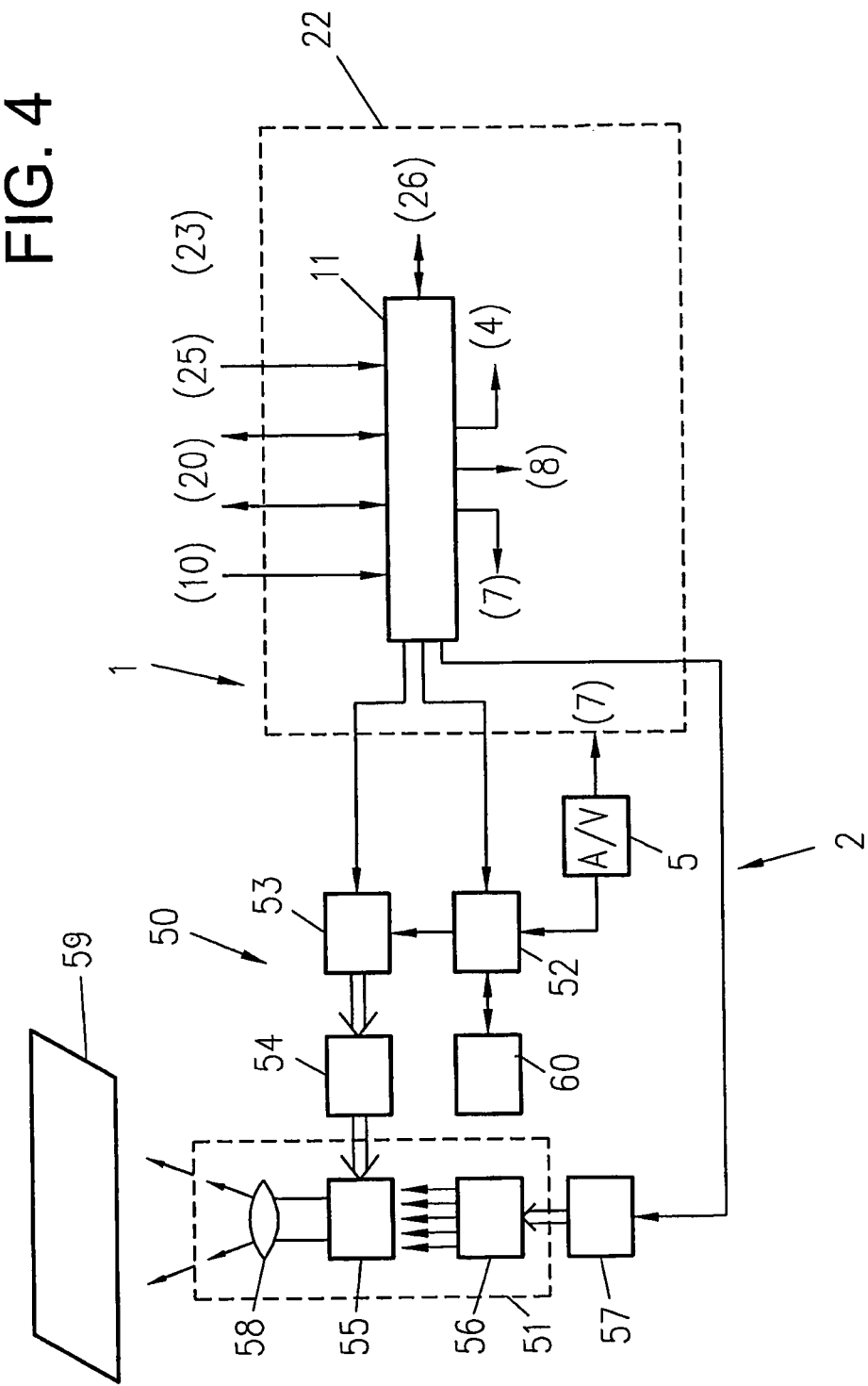
FIG. 4 shows schematically, in the form of a block circuit diagram, the application of the system according to the invention for the additional control of video signal reproduction means, which system is shown in simplified form compared to FIG. 1.

As mentioned, the signal source 5 or generally the device 2 may be a combined audio/video system, that is to say the signal source 5 can output not only audio signals but also video signals or generally image information. The device 2 then contains generally video signal reproduction means 50, as is schematically illustrated in FIG. 4, wherein an embodiment with a video projection system 51 is shown as a concrete example for such video signal reproduction means 50. Instead of a video projection system, also a conventional screen (video screen) can be provided for a video signal reproduction. The term "video signal reproduction means" is thus understood to include, very generally, means for reproducing image or video information, that is video signals in the narrow sense as well as S image data, such as for still images, comparable to a slide projection.

FIG. 4 further shows, besides this video signal reproduction part of the device 2, that is to say the video signal reproduction means 50, also the signal source 5 connected to the control means 22 already explained, especially the control processor means 11, wherein only control inputs and control outputs for the components elucidated further in FIG. 1 are pointed out with their reference numbers, for the sake of simplification and clarity of the drawing.

A video decoding and buffer unit 52 is connected to the signal source, which unit 52 is fed with a video data stream by the signal source 5. A video data processing and scaling unit 53, from which the video data go to an LCD drive 54, which activates LCD panels 55 in the video projection system 51, is connected to this video decoding-and buffer unit 52. Usually, an LCD panel 55 is provided for every primary color. A light source 56 activated through a lamp driver 57 is connected upstream of the LCD panels 55.

The light rays emitted by the LCD panels 55 are directed to a projection surface 59, which can be, for example, the ceiling of a room, through an optical system 58, schematically shown by a lens.

As described so far, this is a conventional structure of video signal reproduction means 50. What is important now is that the video decoding and buffer unit 52, which is further connected to a memory 60, as well as the video data processing and scaling unit 53 and the lamp driver 57 are connected via control terminals to the control means 22, and in concrete terms to the control processor means 11 of these control means 22, thus to make a change possible, especially a slowing-down of the image sequence through the video decoding and buffer unit 52 and brightness control through the video data processing and scaling unit 53, especially in terms of an ever darkening video reproduction. Furthermore, the video signal reproduction is finally terminated through a corresponding control signal that is applied to the lamp driver 57.

It may be observed in this respect that the projection light sources can be dimmed, so that in principle, brightness can be controlled also via the lamp driver 57.

Furthermore, it is clear that also special independent audio and video signal sources, such as a CD player and a video recorder can be present within the device 2.

For the monitoring of the state of relaxation of the person concerned and the derivation of the control signals, a reference may be made to FIG. 1 and the respective previous description.

It may further be observed that it is not absolutely necessary that the heart rate and/or the pulse rate be detected, but also a frequency corresponding to the heart rate and/or the pulse rate can be detected.

The invention claimed is:

1. A system for receiving and controlling reproduction of at least part of a source signal comprising video signals and music signals, via monitoring of a state of relaxation of a person, which system comprises:
a device for receiving the source signal;
sensor means for detecting at least one changeable physiological characteristic of the person, as the person progresses from an awake state into a sleep state, which characteristic assumes different values depending on different sleep phases of the person;
analyzing means for recognizing sleep phases on a basis of the at least one changing physiological characteristic detected by the sensor means and for outputting control information characteristic of the sleep phases; and,
control means, which control means include reproduction-speed control-means, which are arranged for changing a speed for the reproduction of the music signals based on the at least one detected changing physiological characteristic, such that the speed of reproduction is changed to match the physiological characteristic, and which control means are arranged for receiving the control information and terminating the reproduction of the music signals after receiving control information characteristic of a commencing of a certain sleep phase;
wherein the control means are further adapted for activating video signal reproduction means to slow down a speed for the reproduction of the video signals dependent on the at least one detected physiological characteristic.

2. A system as claimed in claim 1, wherein the reproduction speed control means comprise digital signal processor means, which digital signal processor means are arranged for receiving music signals to be reproduced, the music signals containing a rhythm; and for slowing down the music rhythm contained in the music signal dependent on characteristic control information without affecting pitch.

3. A system as claimed in claim 1, wherein the analyzing means are arranged for recognizing a transition from a first deep sleep phase of the person into a first dream phase of the person and delivering control information characteristic of this transition for terminating the reproduction of music signals.

4. A system as claimed in claim 1, wherein the control means are adapted for activating volume control means to reduce loudness during the reproduction of the music signals.

5. A system as claimed in claim 1, wherein the control means are adapted for activating sound control means to change a sound characteristic during the reproduction of the music signals.

6. A system as claimed in claim 1, wherein the control means are adapted for activating the video signal reproduction means to reduce brightness values of the video signals to be reproduced.

7. A system as claimed in claim 1, wherein the sensor means comprise at least one microphone.

8. A system as claimed in claim 7, wherein the sensor means are adapted to detect acoustoelectrically a frequency corresponding to a breathing rate, a pulse rate or a heart rate of the person as a physiological characteristic.

9. A system as claimed in claim 7, wherein the sensor means are adapted to detect acoustoelectrically irregular noises caused by muscle movements.

10. A system as claimed in claim 7, wherein the control means further include automatic speech recognition means that are adapted to recognize predefined control commands and for generating electrical control signals corresponding to at least one of the recognized predefined control commands for controlling the reproduction of the music signals.

11. A system as claimed in claim 1, wherein wireless transmission means are provided and adapted as a transmission path between the sensor means and the analyzing means.

12. The system of claim 1 wherein the source signal is provided on a source selected from the group consisting of CDs, SACDs, RDDs, DVDs, and magnetic tape cassettes.

13. The system of claim 1 wherein the control means are further adapted to effect a gradual transition from an initially full sound pattern of the music signal to damping of high and low frequency components.

14. A system for receiving and controlling reproduction of at least part of a source signal, said source signal comprising an audio presentation comprising music signals, via monitoring of a state of relaxation of a person, which system comprises:
a device for receiving the source signal;
sensor means for detecting at least one changeable physiological characteristic of the person, as the person progresses from an awake state into a sleep state, which characteristic assumes different values depending on different sleep phases of the person;
analyzing means for recognizing sleep phases or, a basis of the at least one changing physiological characteristic detected by the sensor means and for outputting control information characteristic of the sleep phases; and,
control means, which control means include reproduction-speed control-means, which are arranged for changing a speed for the reproduction of the music signals contained in the audio presentation based on the at least one detected changing physiological characteristic, such that the speed of reproduction is changed to match the physiological characteristic and which control means are arranged for receiving the control information and terminating the reproduction of the audio signals after receiving control information characteristic of a commencing of a certain sleep phase;
wherein the reproduction-speed control-means contain flywheel means for generating audio signal reproduction control information, wherein it is possible to pre-define a tempo for the reproduction of the music signals contained in the audio presentation.

15. The system of claim 14 wherein the source signal is provided on a source selected from the group consisting of CDs, SACDs, HDDs, DVDs, and magnetic tape cassettes.

16. The system of claim 14 wherein the control means are further adapted to effect a gradual transition from an initially full sound pattern of the music signal to damping of high and low frequency components.

17. A method for receiving and controlling reproduction of a least part of a source signal, said source signal comprising video signals and audio signals containing music, said method comprising;
receiving the source signal;
monitoring of a state of relaxation of a person, wherein at least one changeable physiological characteristic of the person is detected, as the person progresses from an awake state into a sleep state, which physiological characteristic assumes different values depending upon different sleep phases of the person and wherein sleep phases are recognized on basis of the detected physiological characteristic;
changing speed for the reproduction of the music contained in the audio signals on a basis of the at least one detected physiological characteristic such that the speed of reproduction is changed to match the physiological characteristic; and,
terminating the reproduction of the audio signals when a commencing of a certain sleep phase is recognized;
wherein, in addition to the changed reproduction of sound signals, the speed of the reproduction of the video signals is changed dependent on the at least one detected physiological characteristic.

18. A method as claimed in claim 17, wherein a frequency corresponding to a breathing rate, a pulse rate or to a heart rate of the person is detected as a physiological characteristic.

19. A method as claimed in claim 18, wherein the frequency corresponding to the breathing rate is detected in addition to the frequency corresponding to the pulse rate or the heart rate of the person and detected as a physiological characteristic.

20. A method as claimed in claim 17, wherein irregular noises caused by muscle movements or digestive system are detected as a physiological characteristic.

21. A method as claimed in claim 20, wherein an identifier representing sleep quality of the person is generated on a basis of detected irregular noises caused by muscle movements and optionally based on a time-related course of a pulse rate or a heart rate and/or a breathing rate.

22. A method as claimed in claim 17, wherein slowed-down reproduction of audio signals is terminated upon recognition of a transition from a first deep sleep phase of the person to a first dream phase of the person.

23. A method as claimed in claim 17, wherein a reduction of loudness is effected during reproduction of audio signals.

24. A method as claimed in claim 17, wherein a change in sound characteristics is effected during reproduction of the audio signals.

25. A method as claimed in claim 17, wherein a reduction in brightness values of the video signals to be reproduced is effected.

26. A method as claimed in claim 17, wherein at least one microphone is used for receiving an electro-acoustic signal for detecting the at least one physiological characteristic.

27. A method as claimed in claim 26, wherein the electro-acoustic signal is subjected to an electronic speech recognition procedure, by means of which speech recognition procedure signal sections contained in the electro-acoustic signals and representing acoustic control commands are recognized.

28. The method of claim 17 further comprising effecting a gradual transition from an initially full sound pattern of the music signal to damping of high and low frequency components based upon at least one detected physiological characteristic.

* * * * *